（12）United States Patent
Neto et al.

(10) Patent No.: US 9,023,405 B2
(45) Date of Patent: May 5, 2015

(54) PHARMACEUTICAL COMPOSITION USING STRYPHNODENDRON EXTRACTS FOR TREATING HPV INFECTIONS

(75) Inventors: Manoel Alvaro de Freitas Lins Neto, Maceio (BR); Luiz Carlos Caetano, Maceio (BR); Pedro Accioly de Sa Peixoto Neto, Maceio (BR); Zenaldo Porfirio Da Silva, Maceio (BR)

(73) Assignee: Universidade Federal de Alagoas—UFAL, Maceio (BR)

( * ) Notice: Subject to any disclaimer, the term of this patent is extended or adjusted under 35 U.S.C. 154(b) by 269 days.

(21) Appl. No.: 13/807,560

(22) PCT Filed: Jun. 28, 2011

(86) PCT No.: PCT/BR2011/000205
§ 371 (c)(1),
(2), (4) Date: Sep. 3, 2013

(87) PCT Pub. No.: WO2012/000070
PCT Pub. Date: Jan. 5, 2012

(65) Prior Publication Data
US 2014/0023738 A1    Jan. 23, 2014

(30) Foreign Application Priority Data

Jul. 1, 2010    (BR) ........................................ 000168

(51) Int. Cl.
*A01N 65/00*    (2009.01)
*A61K 36/48*    (2006.01)

(52) U.S. Cl.
CPC ............. *A61K 36/48* (2013.01); *A61K 2236/00* (2013.01)

(58) Field of Classification Search
CPC ......................... A61K 36/00; A61K 2236/333
USPC ......................................................... 424/725
See application file for complete search history.

(56) References Cited

FOREIGN PATENT DOCUMENTS

WO    WO2012000070 A1 *  1/2012

* cited by examiner

*Primary Examiner* — Michael Meller
(74) *Attorney, Agent, or Firm* — Laurence P. Cotton; Smith Risley Tempel Santos LLC

(57) ABSTRACT

The application of extracts, mainly the alcoholic, hydroalcoholic, and aqueous extracts of the bark, bark seam, stem, and seedpod skin of *Abarema cochliocarpos* (Gomes) Barneby & Grimes and/or *Stryphnodendron barbatiman, Stryphnodendron coriaceum* Benth., *S. diacolor* Benth., *S. pulcherrimum* (Wildd) Hoch., *Stryphnodendron adstringens* (Mart.) Coville, *Stryphnodendron obovatum* Benth., *Stryphnodendron polyphyllum* M., and *Pithecellobium avaremotemo* Mart., all popularly known as barbatimão, as adjuvants in pharmaceutical compositions for treatment of infections related to the human papillomavirus (HPV) and cervical cancer prophylaxis.

4 Claims, No Drawings

PHARMACEUTICAL COMPOSITION USING STRYPHNODENDRON EXTRACTS FOR TREATING HPV INFECTIONS

FIELD OF THE INVENTION

The present invention refers to the application of extracts, mainly the alcoholic, hydroalcoholic, and aqueous extracts of the bark, bark seam, stem, and seedpod skin of *Abarema cochliocarpos* (Gomes) Barneby & Grimes and/or *Stryphnodendron barbatiman, Stryphnodendron coriaceum* Benth., *S. diacolor* Benth., *S. pulcherrimum* (Wildd) Hoch., *Stryphnodendron adstringens* (Mart.) Coville, *Stryphnodendron obovatum* Benth., *Stryphnodendron polyphyllum* M., and *Pithecellobium avaremotemo* Mart., popularly known as *barbatiman*, isolated and in mixtures of different proportions of these products and/or together with extract(s) from other natural and/or synthetic sources in the preparation of pharmaceutical compositions, in particular presentations for use at the genital area that can be applied to the vaginal, vulvar, perianal, anal, or penile regions in the form of soaps, dyes, w/o and o/w emulsions (ointments, creams, and gels), aerosols, pastes, ovules, suppository, and the like, for treatment (as adjuvants) of infections related to the human papillomavirus (HPV) and, consequently, for cervical cancer prophylaxis, comprising formulations containing the aforementioned extracts, fractions of these materials and/or chemical component(s), used as active principles and/or pharmacological excipient(s).

The human papillomavirus is a DNA virus of the family Papoviridae, with more than 100 identified types of virus, with some types responsible for vulgar moles, others for anogenital moles and nasopharyngeal papillomas. The HPV does not act on oncogenesis alone; other factors, such as the host's immunological and nutritional status and the use of tobacco and alcohol, also participate together in this process. The HPV reaches the nucleus of basal cells via micro relations with the epithelium, and the first signs of virus genome transcription appear 4 weeks after infection. The incubation period lasts between 3 and 18 months, and the persistence of lesions can be evaluated in weeks, months, or years. As the cell differentiates, antigen production and virus replication on the surface cells increase, and the amount of DNA increases toward the epithelium surface. During this process, genomic proteins and capsid-related structural proteins accumulate.

HPV infection is characterized by apparent, vegetative, vascularized, sessile lesions with multiple papillary projections, designated condyloma acuminata. Most of these lesions are associated with HPV 6 (65%) and 11 (20%); the remaining lesions are associated with less common HPV types. HPV infection occurs more commonly in patients aged between 16 and 25 years. Vaginal lesions caused by HPV can coexist with vulvar moles in 30% of the patients, and over 85% of these patients will have cervical infection.

About *Barbatiman*

*Abarema cochliocarpos*, one of the species popularly known as *barbatiman*, is endemic in Brazil and belongs to the family Mimosaceae. This species is a small to average-sized leafy tree with compound leaves, inflorescence in globose glomeruli, slightly yellow flowers, and greyish white seeds. It is widely employed in natura as a medicinal plant in Brazil (Santos et al., 2007). This plant is popularly known as barbatimão, babatimão, bordão-de-velho (Braga, 1976: p. 89). According to ethnopharmacology, it is used against skin infectious process, as a healing compound, and is also employed to combat leucorrhea and moles (Corrêa, 1984; p. 199, 200).

Several literature works have described the chemical composition of the tannins present in the *barbatiman* barks. The protobinetinidins (Mello & Nahrstetd, 1996), the dimeric proanthocyanidin present in the ketone-soluble extract (Mello et al., 1999), displays anti-inflammatory activity (Lima et al., 1998).

STATE OF THE ART

The treatments described under the state of the art and commonly employed include cytotoxic drugs, surgical procedures, and therapy with different immunomodulatory drugs and can be realized using different drugs as presented below:

a) Desiccant acids: dichloroacetic or trichloroacetic acids are effective on humid lesions of mucous membranes because of the high water content of these tissues. These acids can be directly applied on the moles, preferentially under skin magnification. The rate of local relapses is high—around 30%.

b) Podophyllin: its biological effect is due to its antimitotic action. It has systemic toxic effects—neurological and hepatorrenal toxicity and bone marrow suppression. It is contraindicated during pregnancy. Its application should be restricted to the keratinized skin. The success rate is 20-40% in six months.

c) Focal physical destruction: electrocauterization, cryosurgery, or laser ablation can be employed. These procedures are indicated in the case of persistent skin lesions in which thick keratin prevent penetration of the topical drug. Topical therapy can initially treat condylomatosis; however, primary therapy fails with a secondary relapse rate is approximately 50%. Following treatments will depend of the aspect of the lesion. Vulgar, recurrent, and keratinized moles are better treated using physical destruction methods.

The extended and diffuse picture of warts that grow between treatment sessions respond better to treatment with interferon and continuous topical therapy. The interferons α (derived from leukocytes), β (derived from fibroblasts), and γ (derived from lymphocytes) are used to treat viral infections, and they induce antiviral, antiproliferative, and immunostimulating effects. Intralesion interferon exacerbates the response to topical podophyllin (Douglas et al., 1990); systemic interferon provides added benefits in recurrent juvenile laryngeal papillomatosis (Leventhal et al., 1991) and in the treatment of laryngeal diseases in older patients.

5-fluorouracil (5-FU), it is antimetabolic and is indicated as coadjuvant in the treatment of vaginal condylomatosis, inhibiting the production of ribonucleic acid and DNA. The treatment must be individualized to avoid chronic vaginal ulcerations. Keratinized and flat vaginal lesions do not respond to the treatment as well as classic condylomas. The use of 5-FU has been discontinued due to the high rate of complications, including chronic ulcerations, chemical vaginitis, adenosis, and vulvar vestibulitis. Administration can be topical, intralesional, or parenteral; results vary, and responses are usually dose-dependent. High costs and side effects limit the use of 5-FU.

On the other hand, Imiquimod creams act as modifiers of the immune response, inducing multiple subtypes of interferon-α and of some cytokines, including the Tumoral Necrosis Factor (TNF) and interleukins. This chain stimulates killer cells, T cells, polymorphonuclear cells, and macrophages, enhancing antitumor activity. It is indicated for the treatment of condyloma acuminata of the external and perianal genitalia, and it can be used during pregnancy (class B). Its use in occluded mucous membrane, like vagina and cervix, is outlawed due to the higher absorption of these mucosae. Common side effects associated with the combination with interferon are erythema, itching, scaling, and edema. The cure rate is as high as 50-56%; on rare occasions—in less than 5% of the patients—there are reports of headache, myalgia, and flu-like symptoms.

SUMMARY OF THE INVENTION

As stated, it is urgent that new drugs to treat HPV infections are made available. Therefore, the present instrument of industrial property presents phytotherapic drugs that include the active principles of *Abarema cochliocarpos* (Gomes) Barneby & Grimes and other natural or synthetic substances in their formulations. Pre-clinical and clinical tests were used to evaluate the products proposed in the invention modality presented here. The results of these tests represent a new alternative for the treatment of infections caused by HPV and cervical cancer prophylaxis.

Contrary to the solutions described in the section about the state of the technique, the use of *barbatiman* ointment in the treatment of HPV offers the following advantages: absence of side effects, facile self-application, unrestricted use in children and pregnant women, low local relapse rates (around 11%), and low cost (the raw material is easily found in the Brazilian flora). Moreover, this ointment can be used internally; that is, in the rectal, vaginal, penile, and buccal mucosae without risking side effects.

DETAILED DESCRIPTION OF THE PATENT

1. Obtaining the extracts: Barbatiman (*Abarema cochliocarpos*) barks were dry and crushed in an electric mill (1 Kg) and extracted by maceration with ethanol (92.8° GL) (3 L×2) for 72 h. The resulting ethanolic extract was filtered through filter paper (Watman no. 2) and concentrated to a volume of 0.1 L in a rotary evaporator working at 60° C. A mass of 0.4 kg of the dry extract was obtained, which corresponded to a yield of 35 to 45% (p/p) in relation to the dry weight of the barks and bark seams. The aqueous extract provides a yield of 33% (w/w) while the hydroalcoholic extract (9:1) provides a yield of 38%, using preparation procedures identical to those employed in the case of the hidrated ethanolic extract (92.8° GL).
2. Preparation of the ointment: The ointment was prepared by heating 0.4 L of vegetable oil (canola) and edible paraffin (70 g) in a water bath at 60° C. for 30 min. The concentrated volume of the *barbatiman* alcoholic extract (0.1 L) obtained in item 1 was slowly added to the mixture, which was homogenized manually by using a wooden spoon and making uniform circular movements for 10 min.
3. The container was removed from the water bath, and homogenization was left to proceed for 15 min. The resulting ointment—ready for use—was transferred to five 100-mL plastic containers that should have between 20 and 30% (p/p) of the active principle.

Phytochemical Studies

The phytochemical, toxicological, pharmacological and clinical studies with the *barbatiman* alcoholic, aqueous, and hydroalcoholic extracts are presented below.

Botanical Material Gathering

The *barbatiman* extracts were obtained from the reddish barks and bark seams of the stem and from the skin of mature seedpods. The extracts contained at least 20% (w/w) of tannins. The barks and bark seams were collected from the stem of healthy *Abarema cochliocarpos* plants growing in two different locations: Campus A.C. Simões, UFAL, Maceió, state of Alagoas, Brazil, and Mata Atlântica in the region of Coruripe, state of Alagoas, Brazil. The reddish skin of mature seedpods also contained the studied active principles. A specimen of the plant *Abarema cochliocarpos* was deposited in the herbarium of Instituto do Meio Ambiente do Estado de Alagoas (IMA-AL, Environment Institute of the state of Alagoas) under number mac 8830.

Biological Tests

The biological and microbiological activities of the hydrated alcoholic extract (ethanol 92.8° GL) of the barks and bark seams of *barbatiman* were conducted on *Artemia salina* larvae and four *Candida* species (leveduriform fungi). The assays were conducted in the Laboratório de Química de Produtos Naturais/IQB/UFAL (Laboratory of Natural Products Chemistry of the Chemistry Institute of the Federal University of Alagoas, Brazil) and Laboratório de Microbiologia Aplicada/ICBS/FAL (Laboratory of Applied Microbiology of ICBS of the Federal University of Alagoas, Brazil)

Microbiological Tests

The microbiological tests were carried out using the alcoholic extract of the barks and bark seams of the *barbatiman* stem at a concentration of 100 mg mL$^{-1}$, resuspended in a solution of methanol/water 1:2 (v/v).

To determine the antimicrobial activity, the modified Kirby and Bauer agar diffusion method was employed (MOURA, 1977). The microorganisms were transferred to tubes containing 2 mL of BHI liquid medium and incubated at 37° C., for 24 h. Turbidity indicated bacterial growth. Next, 1 mL of BHI (approximately $10^9$ microorganisms/mL) was added to tubes containing 12 mL of agar Mueller Hinton at a temperature of 45° C., and the content was placed on plates containing a bacteriological agar base with formation of wells (0.7 cm). A control assay was also conducted for each microorganism, using the standard antimicrobial agent—chloramphenicol (30 μg mL$^{-1}$), tetracycline (30 μg mL$^{-1}$), itraconazole (11.6 μg mL$^{-1}$), ketoconazole (11.6 μg mL$^{-1}$), fluconazole (700 μg mL$^{-1}$), and nystatine (350 μg mL$^{-1}$). Then, 40 μL of the ethanolic extract resuspended in methanol/water (1:2) was added to each well. The plates were incubated at 37° C. for 24 h. The halos were measured using halometers. Halos≥10.0 mm indicated antimicrobial activity. All the tests were accomplished in duplicate, and the results were determined using the average inhibition, according to LIMA et al., 2002.

The antimicrobial activity evaluation studies of the extracts were conducted in vitro, using the following microorganisms: Bacteria—*Staphylococcus aureus, Pseudomonas aeruginosa, Enterococcus faecalis, Escherichia coli, Alcaligenes faecalis, Streptococcus pyogenes*, and *Salmonella enteriditis* and Leveduriform fungi—*Candida albicans, Candida tropicalis, Candida krusei*, and *Candida guilliermondi*, all obtained from the fungi collection of the Laboratory of Applied Microbiology—L@MA, ICBS-UFAL.

The hydroethanolic extracts were active against all the assayed microorganisms. In some cases, the results were better than those achieved with the tested antibiotics, as in the case of the *P. aeruginosa* strains BAC 57, BAC 101, BAC 104, BAC 105, and BAC 125.

The hydroethanolic extract gave satisfactory results against 100% of the 12 tested *S. aureus* strains, especially in the case of the multiresistant strains BAC 95 and BAC 97.

The hydroethanolic extract provided the best results against the following strains of leveduriform fungi of the genus *Candida*: *C. albicans* FUN 05 (halo=24 mm), *C. tropicalis* FUN 36 (halo=18 mm), *C. krusei* FUN 11 (halo=24 mm), and *C. guilliermondi* FUN 46 (halo=23 mm).

All the tested extracts were active against *P. aeruginosa, S. aureus*, and fungi of the genus *Candida*. The results attested to the broad antimicrobial spectrum of the barks, pods, and seeds of *A. cochliocarpos* against clinically important microorganisms.

Toxicological Tests

The toxicological tests were accomplished on *Artemia salina* microlarvae and *Mus musculus* mice.

The toxic activity evaluation of the alcoholic extract (92.8° GL), was conducted in saline medium using recently hatched *Artemia salina* leach microlarvae, at concentrations of 10, 100, and 200 μg mL$^{-1}$.

For the conduction of the bioassays it was used the methodology described by Santos Pimenta L P, Pinto G B, Takahashi J A, Silva L G, and Boaventura M A; Biological screening of Annonaceous Brazilian Medicinal Plants using *Artemia salina* (brine shrimp test), *Phytomedicine* 10 (2-3) 209-212, with adaptations. Each solution was assessed in triplicate, using ten *A. salina* larvae. This experiment was performed at room temperature (26-28° C.), under artificial light, for a period of 24 consecutive hours. A control test was carried out using 5 mL of the saline solution and ten *A. salina* larvae under the same experimental conditions as the aforementioned tests. These bioassays showed that the alcoholic extract did not display toxicity at concentrations up to 100 μg mL$^{-1}$.

Sixteen healthy adult male and female *Mus musculus* mice were used for LC$_{50}$ (Lethal Concentration) determination. The mice were weighed in a semi-analytical scale (0.001 g) and divided into four groups. The mice belonging to groups 1, 2, and 3 were intraperitonially inoculated with 70, 75, and 80 μL of the *barbatiman* hydroethanolic extract, resuspended in water at 0.1 g mL$^{-1}$, respectively. The Group 4 (control) was intraperitoneally inoculated with 80 μL of distilled water. The dose that killed 50% of the inoculated mice within 96 h was considered lethal. The dead mice were submitted to autopsy for removal of the liver and spleen, which were weighed on a semi-analytical scale. The mice that remained alive were anesthetized by inhalation of sulfuric ether and, according to the procedure above, their liver and spleen were removed and weighed in a semi-analytical scale.

LC$_{50}$ was found to be 75 μL of the hydroethanolic extract of the barks and bark seams of *barbatiman*—corresponding to a dose of 250 mg Kg$^{-1}$. The tested mice presented a metabolism reduction and tachycardia.

Pharmacological Tests

The pharmacological, preclinical, and clinical evaluations of the *barbatiman* hydroethanolic extract were conducted in vitro and in vivo for the following activities: primary skin irritation, acute ocular irritation, healing capacity, and induction of abortion.

The male and female mice of the species *Mus musculus* used in the experiments were obtained from the biotherium of CCBi/UFAL and CCBS/UFS. The albino rabbits of the New Zealand lineage were provided by the breeding site of the county of Maceió, state of Alagoas, Brazil. The animals were treated for parasites and allowed to acclimatize in the biotherium of CCBi/UFAL.

The primary skin irritation tests were carried out according to BRITO (1994) and consisted in applying the drug onto the integral animal skin. Three albino rabbits were employed. The animals were placed in individual cages at room temperature, in 12-hour dark-light cycle, with animal food (PURINA) and water ad libitum. The rabbits were shaved 24 hours prior to application of the tested compound. Four application sites were defined, two of which were submitted to abrasion. Each rabbit had its own control application site. Using a single dose, 500 μL of the crude ethanolic extract of the barks (0.1 g mL$^{-1}$) were applied in a single dose, on a gauze, that was then placed on the rabbit skin. The gauze compress was fixed with hypoallergic adhesive tape.

The animals exposed to the drugs were housed in separate cages for four hours. At the end of the exposure time, the target skin region was washed with water and observed at 1, 24, and 72 hours after removal of the compress. At the site of drug application, the formation of erythema, scars, or edemas was examined, according to a system employed by the Federal Hazardous Substances Act of the United States of America.

Skin redness, without edema, was detected during the first 60 minutes after gauze removal in the assay involving the scarred skin. The redness had disappeared when the skin was examined after 24 hours of removal of the gauze compress.

According to BRITO (1994), to obtain the degree of skin irritation elicited by a substance, it is necessary to add the subtotal and divide by 4, which corresponds to erythema of the integral and scarred skin and erythema and edema of the integral and scarred skin, which gives the degree of skin irritability of the substance. A degree of 0.25 was obtained, which classifies the substance (0-1) as non-irritant.

The acute ocular irritation test was conducted in order to analyze reversible alterations to the rabbits' eyes originated from instillation of the hydroethanolic extract of *barbatiman* barks.

Four healthy male albino rabbits of the New Zealand lineage were selected for the test. The rabbits were housed in individual cages at room temperature, in 12-hour dark-light cycles, with animal food (PURINA) and water ad libitum. Both eyes of each rabbit were examined 24 hours before application of the tested compound, in order to avoid working with animals that had pre-existing lesions or ocular defects.

The *barbatiman* hydroethanolic extract was resuspended in water at a concentration of 0.1 g mL$^{-1}$, and 100 μL of the extract was instilled into the conjunctiva of the rabbit's right eye, after carefully lifting the lower eyelid of the ocular globe. The rabbits' eyes were not washed during the first 24 hours after instillation of the drug. Distilled water (100 μL) was applied to the left eye of each animal, as control. The fourth rabbit received 100 μL of HCl 1% in the right eye, and the left eye served as control.

The rabbits' eyes were examined 24, 48, and 72 hours after instillation, with the aid of an ophthalmoscope. Macroscopic lesions in the iris, cornea, and conjunctiva were examined and compared with the control eye. The ocular lesions were rated according to an illustrated guidebook on ocular irritation (BRITO, 1994).

According to the tests carried out in vitro, instillation of 100 μL of the *barbatiman* extract at 20% did not elicit any perceptible reaction in the cornea, iris, and conjunctiva as compared with the positive (HCl 1%) and negative (distilled water) controls. The pharmacological tests did not evidence ocular alterations or skin primary irritation.

Thirty-six healthy adult albino rabbits of the New Zealand lineage weighing between 1.250 and 1.700 Kg were used for the healing tests. The animals were shaved and housed in individual cages at room temperature, in 12-hour light-dark cycles, with PURINA animal food and water ad libitum.

The rabbits were anesthetized with local administration of lidocaine hydrochloride and inhalation of sulfuric ether. Four incisions were made on the skin of each rabbit until the subcutaneous layer was reached. A distance of 3 cm was maintained between each incision.

The animals were divided into three groups. The group A, control, received NaCl 0.9% solution during the 14 days of treatment period. Group B was treated with rifamycin and group C received the ethanolic extract of *barbatiman* barks, resuspended in water (0.1 g mL$^{-1}$). The incisions remained open, and the rabbits were treated from the first day of the incision until the 14$^{th}$ day after the incision was made. On the 7$^{th}$ day, pieces were removed from ⅓ of the rabbits and part of the liver for histological analysis, and the animals were then killed. On 14$^{th}$ day, the remaining rabbits were killed, and the pieces and part of the liver were removed for histological analysis.

Macroscopic analyses were accomplished in order to determine the degree of retention scar healing and microscopic analyses in terms of epithelization degree, intensity and type of inflammatory reaction, and presence of neovascularization, as described by ARAUJO et al. (1998).

The incisions treated with *barbatiman*, rifamycin, and sterile saline on a daily basis presented different healing profiles. The *barbatiman* extract displayed better activity until 72 hours of treatment and purulent secretion was not present, which does not happen in tests with rifamycin and saline solution that present purulent secretion.

*Barbatiman* exhibited excellent healing activity, verified mainly during the first 72 hours of treatment, acting better than rifamycin and the saline solution. *Barbatiman* favored disappearance of purulent secretion and favored hyperemia and the appearance of granulation tissue.

To test the abortion induction, twenty-eight healthy adult mice, 21 female and 7 male, were used. One male and three female mice were left to mate for 96 hours. The males were not included in the steps following mating; the females were separated into three groups—eight, eight, and five mice were included in groups 1, 2, and 3, respectively. Group 1 received heated aqueous extract of *barbatiman* barks at a concentration of 0.5% for four days after the mating period, alternating between water (12 hours) and extract (12 hours). Group 2 received the same *barbatiman* extract from day 5 to day 8 after the mating period, alternating between water (12 hours) and extract (12 hours). Group 3 constituted the control and received only water throughout the experiment.

The mice were weighed during the experiment. On day 20 after mating, the pregnant mice were anesthetized with sulfuric ether and placed on the surgical table in supine position, to facilitate surgical incision. An infra-umbilical median longitudinal laparotomy was carried out. Using a pair of scissors and a pair of dissection tweezers, the skin and muscle of the abdominal wall were lifted after the incision. The peritoneum was opened, showing the whole abdominal cavity, and the number of uterine implants and reabsorptions was counted.

*Barbatiman* ingestion by pregnant mice did not alter the fertility or the implant index. Therefore, *barbatiman* does not alter the initial cell division mechanisms or interferes in the implantation processes.

Pre-Clinical Trials

The gel or ointment containing the *barbatiman* extract was tested on the ocular globe of test animals using the method described by Draize J H (1956) The skin game. *International Record of Medicine and General Practice Clinics*, 169 (1), p. 37-39. The irritation score was equal to zero, which corresponds to a non-irritant product. The antiedematous activity of this product was tested using the carrageenan rat paw edema model; the product had effect similar to that of dexamethasone, without the collateral effects of this drug.

Compared with the standard treatment (fibrinolysin+deoxyribonuclease+chloroamphenicol), the healing activity of the *barbatiman* hydroethanolic extract, formulated as cream, was evident in the open wound model healing test. The tests using the ointment led to formation of a thick scab, which reduced irritability, pain, and light bleeding.

Clinical Evaluation of the *Barbatiman* Extracts

The clinical studies on the *barbatiman* extracts showed their anti-inflammatory and healing action in women with cervicitis and cervicovaginitis. This pharmacological action was demonstrated by clinical practice in folk medicine. Recent studies on the clinical and biopharmaceutical aspects of *barbatiman* extracts revealed its efficient action in vaginitis, cervicitis, and cervicovaginitis as compared with standard drugs—*barbatiman* extracts led to disappearance of discharge, unpleasant odor, itching, and pain in a significant number of patients with these gynecologic conditions.

The ointment containing 20% (w/w) of the *barbatiman* hydroethanolic extract, offered free of charge, was topically applied twice a day, for 60 days. The patients were examined every 15 days (a total of 2 visits per patient enrolled in the study). On these visits, a macroscopic evaluation was conducted, in order to verify the possible therapeutic effect of the extract on perianal, vulvar, and penile lesions.

This work consisted of a prospective study. Fifty male and female patients aged between 21 and 50 years, with clinical diagnosis for condyloma acuminatum (HPV), assisted at the Proctology outpatient clinic of the University Hospital of the Federal University of Alagoas (UFAL), Brazil, between October 2002 and September 2009, and were included in the study. All the lesions were photographed at the beginning, during, and at the end of the period proposed for treatment. The patients were informed about the work and agreed to participate. All the patients were followed up; lesions disappeared in 45 patients, the other patients quit the study and did not return to the clinic. Forty-five patients saw total regression of the lesions, without relapse. In general clinical evaluation of the phytotherapic, compound, it can be concluded that the product afforded highly significant clinical results in the treatment of infections by HPV.

The invention claimed is:

1. A method of treating a human suffering from a human papillomavirus infection, comprising administering to said human a therapeutically effective amount of an extract of *Abarema cochliocarpos* to effectively treat the human papillomavirus infection in said human.

2. The method of claim 1, wherein said extract is a hydroalcoholic extract.

3. The method of claim 2, wherein said therapeutically effective amount is at least about 20% (w/w) of an extract of *Abarema cochliocarpos*.

4. The method of claim 1, wherein said extract is prepared as an ointment.

* * * * *